(12) United States Patent
Nagata

(10) Patent No.: US 8,012,940 B2
(45) Date of Patent: *Sep. 6, 2011

(54) UTILIZATION OF ANTI-NEUROPATHIC PAIN EFFECT OF D-ALLOSE AND D-PSICOSE

(75) Inventor: Mitsuhiro Nagata, Kagawa (JP)

(73) Assignees: Teikoku Seiyaku Co., Ltd., Higashikagawa-shi (JP); National University Corporation Kagawa University, Takamatsu-shi (JP)

( * ) Notice: Subject to any disclaimer, the term of this patent is extended or adjusted under 35 U.S.C. 154(b) by 750 days.

This patent is subject to a terminal disclaimer.

(21) Appl. No.: 11/995,974

(22) PCT Filed: Jul. 20, 2006

(86) PCT No.: PCT/JP2006/314363
§ 371 (c)(1),
(2), (4) Date: Jan. 17, 2008

(87) PCT Pub. No.: WO2007/010973
PCT Pub. Date: Jan. 25, 2007

(65) Prior Publication Data
US 2009/0264374 A1    Oct. 22, 2009

(30) Foreign Application Priority Data

Jul. 20, 2005  (JP) .................. 2005-209492
Jul. 19, 2006  (JP) .................. 2006-196750

(51) Int. Cl.
*A01N 43/04* (2006.01)
*A61K 31/70* (2006.01)

(52) U.S. Cl. ....................................... 514/23
(58) Field of Classification Search ........... None
See application file for complete search history.

(56) References Cited

U.S. PATENT DOCUMENTS

2005/0074819 A1 * 4/2005 Inoue et al. .................. 435/7.2
2005/0245459 A1   11/2005 Izumori et al.

FOREIGN PATENT DOCUMENTS

| JP | 2003529570 A | 10/2003 |
| JP | 2004537494 A | 12/2004 |
| JP | 2005-263744 A | 9/2005 |
| JP | 2005263734 A | 9/2005 |
| WO | 03097820 A1 | 11/2003 |
| WO | 2006093292 A1 | 9/2006 |

OTHER PUBLICATIONS

Wesselman. Surgical Management of Pain. Burchield. Thieme Medical Publishers, Inc., New York 2002.*
International Search Report of PCT/JP2006/314363, date of mailing Oct. 24, 2006.

* cited by examiner

*Primary Examiner* — Layla Bland
(74) *Attorney, Agent, or Firm* — Westerman, Hattori, Daniels & Adrian, LLP

(57) ABSTRACT

To control neuropathic pain produced by various mechanisms. Disclosed is a composition for elimination, relief or reduction of neuropathic pain comprising, as an active ingredient, at least one substance selected from the group consisting of D-allose, a derivative of D-allose, D-psicose and a derivative of D-psicose preferably in an amount of 0.01 to 90% by weight. The composition may comprise a mixture of D-allose and/or a derivative thereof and D-psicose and/or a derivative thereof at a ratio of 1:1 to 10:1. The neuropathic pain may be one induced by a disease selected from the group consisting of trigeminal neuralgia, postoperative pain, periodontitis, gingivitis, gingivostomatitis, oral ulcer, herpes zoster, postherpetic neuralgia, diabetic neuritis, causalgia, phantom limb pain and malignant tumor. Also disclosed is use of the composition for elimination, relief or reduction of neuropathic pain by administering the composition to a patient with neuropathic pain in such an amount that 0.01 to 100 g of the at least one substance can be taken by the patient per day.

4 Claims, 3 Drawing Sheets

UTILIZATION OF ANTI-NEUROPATHIC PAIN EFFECT OF D-ALLOSE AND D-PSICOSE

TECHNICAL FIELD

The present invention relates to the utilization of the effects of one type of rare sugars, namely D-allose and/or derivatives thereof as well as D-psicose and/or derivatives thereof, on neuropathic pain.

More specifically, the invention relates to a composition containing any single one or a mixture of D-allose and/or derivatives thereof and D-psicose and/or derivatives thereof as the active ingredient, which is capable of suppressing neuropathic pain induced by various causes and is also capable of controlling pains due to trigeminal neuralgia, neuralgia during affliction with herpes zoster and/or after affliction with herpes zoster, post-surgery pain, diabetic neuritis, causalgia, and phantom lib, and which is suitable for patients with such diseases. The composition includes for example food products, foodstuff materials, food additives, drinks, drinking water, pharmaceutical agents, raw materials for pharmaceutical preparations, and feeds. Additionally, the invention relates to a method for controlling neuropathic pain induced by various causes, by using the composition comprising any single one or a mixture of D-allose and/or derivatives thereof and D-psicose and/or derivatives thereof.

BACKGROUND ART

Rare sugars are monosaccharides existing at very slight amounts in the natural kingdom. Rare sugars are grouped in aldoses, ketoses and alcohols, depending on the chemical structures. The aldoses include for example D-allose; the ketoses include for example D-psicose; and the alcohols include for example allitol.

Because most of such sugars were hardly available since the mass production thereof was not achieved, almost no research works about the physiological activities and pharmacological activities thereof were done. A method for producing the sugars at a mass scale has been developed recently by Izumori, et al., in the Agricultural Department, the National University Corporation Kagawa University, so that research works about the biological activities thereof are now under way. In vitro experiments with leukocyte, an action of suppressing active oxygen generation has been found in D-allose, while in D-psicose, an active oxygen-scavenging action and MCP-1 secretion-suppressing action have been found at similar experiments (patent reference 1).

Neuropathic pain is a pain without any stimulation of peripheral sensory receptors and is a chronic pain caused by the direct damages and pressurization of nerve tissues as induction factors. Pain induced by malignant tumor, diabetic neuralgia, herpes zoster and the like is a typical neuropathic pain. Additionally, pain occurring one to 6 months after the incidence of bone fracture, injuries, and burn is also classified as neuropathic pain. The symptoms are spontaneous pains sustaining or emerging spontaneously, involving abnormal sensations such as numbness, electric current shock, minced-up feeling and biting, hyper-sensitivity against algesthesia and allodynia. The mechanism of the occurrence is not known. As hypotheses, there are suggested for example the disorders of the blood nerve barrier, abnormal synapse formation in lumber spinal dorsal horn cells, the abnormal regeneration of demyelinated fiber, the increase of receptor sensitivity, and the abnormal distribution of sympathetic nerve fiber. Specific diseases with neuropathic pain include for example trigeminal neuralgia, postherpeutic neuralgia, pain after traumatic peripheral nerve damages, painful diabetic neuropathy, and pain after arm neuroplexus is pulled out and damaged, and additionally include for example phantom limb pain, and pains due to spinal diseases, injuries, multiple-sclerosis, syringomyelia, spinal cord tumor, and brain cancer, and still more additionally include cancer pain for which analgesic effects with narcotic analgesics such as morphine are insufficiently effective.

Therapeutic treatment (amelioration) represents the effect of suppressing pain emerging in a neuropathic fashion, through the administration of a drug after nerve damages, and also represents the effect of mitigating pain or eliminating pain by allowing the abnormalized pain threshold to be back around the normal level.

Therapeutic treatment (amelioration) represents the effect of suppressing pain emerging in a neuropathic fashion, through the administration of a drug after nerve damages, and also represents the effect of mitigating pain or eliminating pain by allowing the abnormalized pain threshold to be back around the normal level.

The countermeasure against neuropathic pain at clinical practice is insufficient, unfortunately. A therapeutic method for such diseases includes a nerve blocking therapy using local anesthesia. However, such therapeutic method is almost never effective for cases with the diseases sustained for a long period of time. Additionally, the therapeutic treatment itself should disadvantageously be continued for a prolonged period of time. Further, various analgesics have been attempted. However, almost not any effective analgesics have been developed. In recent years, meanwhile, attention has been focused on pharmaceutical therapies, so that examinations about tricyclic antidepressants (amitriptyline, imipramine, and nortriptyline), gabapentin, mexiletine, clonidine, ketamine, opioide (morphine, fentanyl) and drugs for local administration such as capsaicin are made for their actions of mitigating the pain of neuropathic pain. It has been shown that thalidomide mitigates neuropathic pain by preventing the damage of the blood nerve barrier. Therefore, an outcome in future will be expected. However, these drugs are now held at experimental stages, so some clinically verified effect cannot be expected. Further, it has been known that analgesics effective for general nonceptive pain, particularly narcotic analgesics are hardly effective for neuropathic pain. For example, morphine has a strong analgesic action for noniceptive pain but morphine is hardly effective for neuropathic pain (non-patent reference 1).

Non-patent reference 1: The Lancet 353, 1959-1966, 1999

Patent reference 1: International Patent Publication No. WO 03/097820

DISCLOSURE OF THE INVENTION

Problems that the Invention is to Solve

Common analgesics such as morphine are hardly effective for chronic pain (neuropathic pain) emerging due to nerve damage because of cancer progress, diabetic mellitus, infections and the like. Cancer is now listed as one example thereof. Analgesics (morphine, etc.) are effective for pain (noniceptive pain) caused by the stimulation of sensory nerve with the cancer itself. By oral administration, analgesics can considerably mitigate the pain. For stronger such pain, analgesics are injected. When cancer progresses to initiate the damage of sensory nerve, neuropathic pain occurs, for which analgesics are hardly effective. For such pain, invasive mitigation therapies such as nerve blocking are attempted. Besides, auxiliary therapies such as auxiliary analgesic agents, radiation therapy and physicotherapy are used in combination at any of the stages. However, nerve blocking has adverse effects, causing complications. Thus, all patients with strong such pain cannot always reach a desired state via nerve block. Even when the pain is eliminated, functional disorders may sometimes emerge. Other than nerve blocking, for example, the change of the dosing route of analgesics and the combined use with auxiliary analgesics are provided as a selection for the therapy. Modern clinical practice is based on the consideration that the quality of life is important. Hence, now, attention has been focused on allowing clinicians to provide accurate information about the outcome expected from each therapy and the advantage and disadvantage thereof after clinicians resolve the erroneous acknowledgement and prejudice of a patient or his or her family. Additionally, attention has now been focused on the selection of a more effective approach not only based on the assessment of the pain but also based on the individual status and the individual sense of values.

The research group of Inoue, et al. in the National Institute of Health Sciences elucidated at the following experiments in rat that the P2X4 receptor as one of the ATP receptors in intramedullary microglia cells was involved in the pain signal transmission. The researchers demonstrated that in the spinal cord of a rat damaged of the cells of the sensory nerve, the P2X4 receptor existed at a high density in the activated microglia cells responsible for intracerebral immunity and that under the suppression of the function of the receptor, the neuropathic pain reaction in the rat was reduced. When activated microglia stimulated with ATP was directly injected into the spinal cord of a normal healthy rat, the rat was adversely more sensitive to pain. The research works showed a possibility that the inhibition of the function of the P2X4 receptor might lead to a development of an innovative therapeutic method of neuropathic pain (M. Tsuda, Y. Shigemoto-Mogami, S. Koizumi, A. Mizokoshi, S. Kohsaka, M. W. Salter & K. Inoue, Nature (2003) 424:778-783) However, the therapy of neuropathic pain via the inhibition of the P2X4 receptor is just shown as a theoretical possibility. The therapy has not yet reached any state of practical application.

Neuropathic pain represents an abnormal state where a contact without absolutely any pain in general or temperature change is felt as pain or a stimulation without any sense of pain in general is felt as pain, so individuals with neuropathic pain have extremely low levels of QOL (quality of life). It is considered that neuropathic pain occurs via some nerve damage. Plural mechanisms are suggested for the onset. Conditions emerging are so complex that definite therapeutic methods have not yet been achieved (Current neuropathic pain, Yuge Takefumi and Moriwaki Katsuyuki, Anesthetic Department Clinical (masui-ka shinryo) Practice 6, Current Neuropathic pain, 2002, Kobundo). In such status, it is currently suggested that the development of therapeutic types as many as possible to cope with each condition is the best coping method with neuropathic pain. For that purpose, the development of drug types with different properties as many as possible as analgesics is required therefor. Many types of drugs for example steroids, nonsteroidal anti-inflammatory drugs, ion channel agonists and antidepressants have been developed so far as analgesics. However, the effects thereof are limited. Adverse actions thereof are also problematic. On the other hand, any sugar with a specific pharmacological action has not been found yet. Almost no sugars have been used as the therapeutic agents therefor.

In screening for an analgesic effect in rare sugars with almost unknown pharmacological properties, the present research works have been done to examine whether or not D-psicose and D-allose have any effect on neuropathic pain.

Based on the research works, it is an object of the invention to provide a composition, a food product, a food product for patients, a foodstuff material, a foodstuff material for patients, a food additive, a food additive for patients, a drink, a drink for patients, a drinking water, a pharmaceutical agent, a raw material for pharmaceutical preparation, a feed and a feed for use during pain, where these are capable of ameliorating the QOL of a patient with neuropathic pain involving various conditions by mitigating and reducing pain and are therefore suitable for such patients and these contain any single one or a mixture of D-allose and/or derivatives thereof and/or D-psicose and/or derivatives thereof.

Additionally, it is an object of the invention to provide a method for controlling neuropathic pain occurring via various mechanisms by using a composition containing any single one or a mixture of D-allose and/or derivatives thereof and/or D-psicose and/or derivatives thereof.

Means for Solving the Problems

The present inventor found that D-allose and D-psicose were effective for neuropathic pain and additionally found that a combined use of these rare sugars enhanced the analgesic effects interactively. Thus, the invention has been achieved. It has been elucidated that active oxygen is involved in diverse diseases, in particular pain and inflammation. Since D-allose and D-psicose are observed at in vitro experiments to have an active oxygen generation-suppressing action and an active oxygen-scavenging action, a possibility of the emergence of an analgesic effect from such rare sugars can be suggested. However, no examination about the efficacy thereof in experimental animal models of neuropathic pain has been made so far. The inventor has made an examination about the effects of D-allose and D-psicose on naturopathic pain occurring in the experimental animal. The inventor has found an effect of these rare sugars on reducing experimental neuropathic pain. Based on the finding, investigations have been done. Thus, the invention has been achieved. Specifically when D-allose and D-psicose were individually given singly to a Chung model as a rat neuropathic pain model, the sugars exerted relatively strong analgesic effects in a short time. Additionally when these rare sugars were both administered in combination, the sugars exerted an effect such that the individual analgesic effects were enhanced interactively.

The invention relates to a composition containing one or more substances selected from the group consisting of D-allose, D-allose derivatives, D-psicose and D-psicose derivatives as the active ingredients for eliminating, mitigating or reducing neuropathic pain.

The invention also relates to a composition containing one or more substances selected from the group consisting of D-allose, D-allose derivatives, D-psicose and D-psicose derivatives as the active ingredients, at 0.1 and 50% by weight for eliminating, mitigating or reducing neuropathic pain, where the composition contains a mixture of D-allose and/or D-allose derivatives and a mixture of D-psicose and/or D-psicose derivatives, at 0.1 to 50% by weight.

The invention also relates to a composition containing one or more substances selected from the group consisting of D-allose, D-allose derivatives, D-psicose and D-psicose derivatives as the active ingredients, at 0.1 and 50% by weight for eliminating, mitigating or reducing neuropathic pain, where the composition contains a mixture of D-allose and/or a D-allose derivative and a mixture of D-psicose and/or a D-psicose derivative, at a ratio of 1:1 to 10:1.

The invention relates to any of the compositions for eliminating, mitigating or reducing neuropathic pain, as described above, where the daily dose of one or more substances selected from the group consisting of D-allose, D-allose derivatives, D-psicose and D-psicose derivatives is 0.01 to g.

The invention also relates to any of the compositions for eliminating, mitigating or reducing pain as described above, where the neuropathic pain is a neuropathic pain due to a disease selected from the group consisting of trigeminal neuralgia, post-surgery pain, periodontitis, gingivitis, gingivostomatitis, oral ulcer, herpes zoster, postherpeutic neuralgia, diabetic neuralgia, causalgia, phantom limb pain and cancer pain.

The invention also relates to any of the compositions for eliminating, mitigating or reducing pain as described above, where the neuropathic pain is a neuropathic pain due to a disease selected from the group consisting of trigeminal neuralgia, post-surgery pain, periodontitis, gingivitis, gingivostomatitis, oral ulcer, herpes zoster, postherpeutic neuralgia, diabetic neuralgia, causalgia, phantom limb pain and malignant tumor.

The invention also relates to a method for eliminating, mitigating or reducing neuropathic pain by using any of the compositions described above, comprising administering one or more substances selected from the group consisting of D-allose, D-allose derivatives, D-psicose and D-psicose derivatives at a daily dose of 0.01 to 100 g to a patient afflicted with neuropathic pain.

ADVANTAGES OF THE INVENTION

In accordance with the invention, there can be provided a novel pharmaceutical product or food composition capable of mitigating neuropathic pain, for which no appropriate therapeutic approach has existed so far. Therefore, the invention will possibly give a great benefit to patients with chronic pain, which emerges due to nerve damages with for example advanced cancer, diabetic mellitus and infections. For these pains, so far, there has never been any approach with efficacious and secure effects for mitigating such pains.

In accordance with the invention, the neuropathic pain involving various conditions can be mitigated and reduced, and there can be provided compositions, food products, food products for patients, foodstuff materials, foodstuff materials for patients, food additives, food additives for patients, drinks, drinks for patients, drinking water, drinking water for patients pharmaceutical agents, raw materials for pharmaceutical preparations, feeds and feeds for use during pain, all of which contain any single one or a mixture of D-allose and/or derivatives thereof and D-psicose and/or derivatives thereof as the active ingredient.

In accordance with the invention, it is provided a method for mitigating and reducing neuropathic pain, using a composition containing any single one or a mixture of D-allose and/or derivatives thereof and D-psicose and/or derivatives thereof as the active ingredient.

BEST MODE FOR CARRYING OUT THE INVENTION

Figure 1:
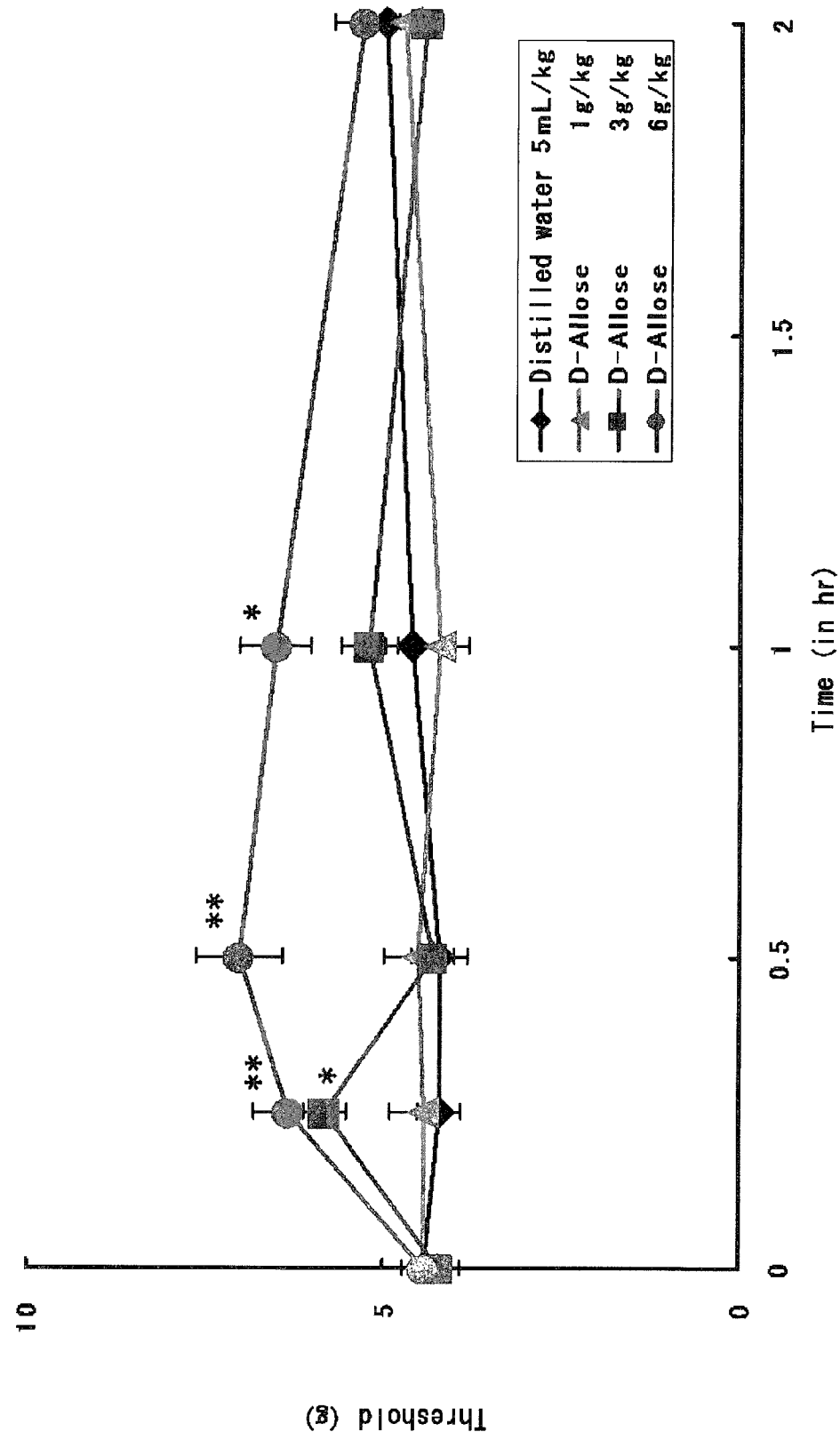
FIG. 1 Effect of D-allose on the pain threshold in the Chung model rat [in the figure, * means $p<0.05$; ** means $p<0.01$ (vs distilled water 5 mL/kg), N=10]

Descriptions are now made about D-allose and D-psicose. D-Allose and D-psicose are monosaccharides existing slightly in the natural kingdom, and are called rare sugar. No reports tell about the toxicity of these rare sugars in humans, so it is considered that the toxicity thereof is low in animals. Although it cannot necessarily be said that the taste of D-allose crystal is good, other substances in mixture with D-allose can easily mask the taste. For example, D-psicose itself has refreshing sweetness and moisture. When mixed with D-allose, D-psicose can mask the taste of D-allose.

Additionally, these rare sugars are readily soluble in water. Since D-allose and/or derivatives thereof and D-psicose and/or derivatives thereof individually have an action of enhancing the individual effects of mitigating and reducing neuropathic pain interactively, the combined used of these two types of rare sugars (including derivatives thereof) is a very preferable method for carrying out the invention.

The composition as the subject of the invention (food products, food products for patients, foodstuff materials, foodstuff materials for patients, food additives, food additives for patients, drinks, drinks for patients, drinking water, pharmaceutical agents, raw materials for pharmaceutical preparations, feeds and feeds for use during pain) may be any edible or pharmaceutical composition containing any single one or a mixture of D-allose and/or derivatives thereof or D-psicose and/or derivatives thereof.

In the composition of the invention in case that the composition contains D-allose and/or derivatives thereof and/or D-psicose and/or derivatives thereof, D-allose and/or derivatives thereof and/or D-psicose and/or derivatives thereof are blended and contained, to 0.1 to 50% by weight in the composition. The sugars are contained at preferably 5 to 40% by weight, more preferably 10 to 30% by weight. When D-allose or D-psicose is at less than 0.1 by weight, the effect of mitigating and reducing neuropathic pain is not sufficient. Above 50% by weight, it is not preferable in an economical standpoint.

D-allose and/or derivatives thereof and D-psicose and/or derivatives thereof are blended at a mixing ratio of D-allose and/or derivatives thereof and D-psicose and/or derivatives thereof in the mixture to 1:1 to 10:1. The mixing ratio is preferably 2:1 to 8:1, more preferably 3:1 to 5:1. When the ratio of D-allose and/or derivatives thereof is smaller than the ratio of D-psicose and/or derivatives thereof, the effect of the latter on enhancing the effect of the former is weakened.

Food products for patients in accordance with the invention are now described. As described above, diseases with neuropathic pain include many diseases for example trigeminal neuralgia, postherpeutic neuralgia, post-surgery pain, diabetic neuralgia, causalgia, and phantom limb pain. These diseases can hardly be therapeutically treated. For the diseases, only a small number of therapeutic agents are effective. By incorporating, ingesting or drinking the composition of the invention as a food product for patients together with general diets, the composition can reduce the pain from these diseases to raise the QOL of the patient. The composition can also reduce the amount of therapeutic agents to be used therefor.

The foodstuff materials and the food additives in accordance with the invention are now described. Because D-allose and D-psicose are highly soluble in water, it is very easy to add such foodstuff materials and such food additives as active ingredients to drinks such as coffee and juice, confectioneries and various processed food products, so the foodstuff materials and the food additives can be used as food additives or foodstuff materials for producing various food products.

When D-allose and/or derivatives thereof and D-psicose and/or derivatives thereof are ingested by humans, the dosage regimen and the dose should be determined in a manner dependent on the age, body weight and symptoms of an individual. In many cases, the effective dose is 0.01 to 100 g per day in dividend doses before meal, after meal or during meal, in case that D-allose and/or derivatives thereof and D-psicose and/or derivatives thereof are individually used singly.

The dosage form of the composition in accordance with the invention for the purpose of reducing neuropathic pain includes for example tablets, capsules, solids such as powder or granule to be dissolved in drinks, semi-solids such as ointments, patches or jellies, liquids such as drinking water, and solutions at high concentrations for use after dilution. Furthermore, the composition of the invention may be added to an appropriate food product to prepare a health food or a diet for patients, for the purpose of analgesic actions.

The drinking water of the invention is now described below. Neuropathic pain involves diverse conditions. Therefore, the therapeutic treatment thereof is hard. A great number of therapeutic agents of neuropathic pain are currently used. However, any of such therapeutic agents has just limited effects, involving adverse actions. Therefore, continuous use thereof for a long term frequently involves risks such as the reduction of the analgesic effects or the occurrence of adverse actions. Hence, a pharmaceutical agent therefor involving no reduction of the effect even after the continuous use for a long term with a rare occurrence of adverse actions has been desired. The drinking water of the invention is a colorless and transparent, odorless aqueous solution with almost no taste, containing any single one or a mixture of D-allose and/or derivatives thereof and D-psicose and/or derivatives thereof at 0.1 to 5% by weight, preferably 1 to 4% by weight, more preferably 2 to 3% by weight. At less than 0.1% by weight, the resulting aqueous solution has an insufficient effect on the suppression of glucose increase. Above 5% by weight, the resulting aqueous solution is never tasteless. The drinking water is colorless and transparent, without any odor and with slight sweetness. Thus, the aqueous solution can be drunk as it is as a drinking water and additionally, the aqueous solution can be used for cooking rice, other cooking, and serving tea and coffee.

By using the drinking water of the invention for preparing daily diets and favorite foods in such manner, neuropathic pain can be controlled with no specific attention. Additionally, a burdensome work of continuous dosing of the pharmaceutical agent can be avoided, while the dose of such pharmaceutical agent can be reduced. In such manner, the occurrence of adverse actions of therapeutic agents for neuropathic pain in current use can be reduced, which enables a long-term administration of the pharmaceutical agent. This is very advantageous for improving the QOL of persons afflicted with neuropathic pain.

The pharmaceutical agent of the invention is now described below. The inventor made detailed examinations about the effects of any single one or a mixture of D-allose and D-psicose on neuropathic pain, using experimental animals.

Consequently, the inventor found that D-allose and D-psicose had an action of suppressing neuropathic pain and that the combined use of D-allose and D-psicose enhanced the effects of single one of them. The action indicates a significant possibility that a novel pharmaceutical agent for mitigating or reducing various neuropathic pains in humans and a novel analgesic method can be created.

When the compound of the invention is to be administered, the compound is preferably administered as an oral agent. Furthermore, the compound can be made into a pharmaceutical preparation in the pure form or in the form of an appropriate pharmaceutical composition, for an appropriate dosing route acceptable for pharmaceutical agents for similar uses. The pharmaceutical agent for the purpose of the effects described above, containing as the active ingredient any single one or a mixture of D-allose and/or derivatives thereof and D-psicose and/or derivatives thereof, may be used as it is. Additionally, the pharmaceutical agent may be blended with appropriate additives such as general excipients, stabilizers, preservatives, binders, and disintegrators and then be prepared into a formulation of a dosage form selected from liquids, capsules, granules, pills, powders, tablets, external agents and jellies, for oral, intravenous, intranasal or transdermal administration.

For clinically applying the composition of the invention as a pharmaceutical agent, the composition is preferably prepared as a pharmaceutical preparation containing any single one or a mixture of D-allose and/or derivatives thereof and D-psicose and/or derivatives thereof as the active ingredient, together with pharmaceutical carriers in solids, semi-solids or liquids, such as additives for example diluents, excipients and stabilizers.

The ratio of the active ingredient to the carrier components is variable between about 1 to 90% by weight. As the dosage form and the dosing regimen, the pharmaceutical agent may be orally dosed as oral agents such as granules, fine granules, powders, tablets, capsules, pills, liquids and jellies. Otherwise, the pharmaceutical agent may orally be given as the drug power. Besides, the pharmaceutical agent is prepared as dosage forms such as external agents such as ointments and patches, for transdermal administration. For use as a liquid, the pharmaceutical agent may be given intravenously or intranasally other than orally.

Carriers, dissolution agents or diluents in organic or inorganic solids, semi-solids or liquids for pharmaceutical use, which are suitable for oral administration, intravenous administration, intranasal or transdermal administration, may be used for preparing the composition of the invention into a pharmaceutical agent.

All of water, gelatin, lactose, starch, magnesium stearate, talc, animal and vegetable oils, benzyl alcohol, gum, polyalkylene glycol, petroleum resins, coconut oil, lanolin and other carriers (carriers) for pharmaceutical use can be used as the carriers for the pharmaceutical agent containing the composition of the invention.

Additionally, stabilizers, emollients, emulsifiers, and salts for modifying osmotic pressure or retaining pH suitable for blended agents may also be used appropriately as auxiliary pharmaceutical agents.

The pharmaceutical agent containing the composition of the invention may contain other pharmaceutically active components to be appropriately given along with the pharmaceutical agent of the invention, for example other appropriate analgesics and anti-inflammatory agents for therapeutic treatment of diseases with neuropathic pain.

In case of granules, fine granules, capsules, powders, tablets, ointments or patches, the composition of the invention is preferably contained at 0.1 to 50% by weight. For liquids, preferably, the corresponding amount (ratio) is at 0.1 to 50% by weight.

The raw materials for pharmaceutical preparation in accordance with the invention are now described below. For producing other appropriate therapeutic agents for neuropathic pain, any single one or a mixture of D-allose and/or derivatives thereof and D-psicose and/or derivatives thereof may be used as the raw material for preparing a pharmaceutical preparation for the purpose of general excipients, stabilizers, preservatives, binders and disintegrators.

In case of the occurrence of secondary neuropathic pain, meanwhile, pain control in addition to the therapeutic treatment of the etiological disease is needed. For producing a therapeutic agent of the etiological disease in such case, the composition of the invention may be used as such a raw material for pharmaceutical preparation as described above. The amount of any single one or a mixture of D-allose and/or derivatives thereof and D-psicose and/or derivatives thereof to be used and the ratio thereof to other appropriate therapeutic agents for neuropathic pain can be adjusted, appropriately, depending on the content of these therapeutic agents in the pharmaceutical preparation or on the properties thereof.

For oral dosing, the clinical dose per day is 0.01 to g, preferably 0.1 to 60 g as D-allose and/or derivatives thereof and D-psicose and/or derivatives thereof per 60-kg body weight of an adult for internal administration. The dose may be appropriately raised or lowered, depending on the age, symptoms and the like. The pharmaceutical agent at the daily dose in accordance with the invention is preferably given once daily or in two dividend doses at an appropriate interval per day, before meals, after meals or during meals.

[Actions]

The D-allose and D-psicose singly given orally to the Chung model as a rat neuropathic pain model exerted a relatively strong analgesic effect in a short time. The combined use of both of these rare sugars enhanced the analgesic effects interactively.

The invention is now described in detail in the following Examples and Test Examples. However, the invention is never limited by them.

EXAMPLE

Experimental Method

Male SD rats of age 6 weeks were divided into groups, each group consisting of 10 rats. So as to examine the effect of a test substance on neuropathic pain, the Chung model was prepared. Specifically, unilateral 5-th and 6-th lumbar pulp nerves of the lumbar pulp nerves were completely knotted at a site as close as possible to lumbar vertebrae. After a 10-day recovery period, the von Frey test was done on the footpad on the surgery side, to measure the pain threshold. The von Frey test was done three times at a 1-week interval as drug holiday. At the first test, the effect of D-allose on the pain threshold was examined; and at the second test and the third test, the effects of D-psicose and a mixture of D-allose and D-psicose on the pain threshold were examined.

The test substances were all dissolved in distilled water. The dose in volume was 5 mL/kg for oral administration. The pain threshold was measured immediately before the administration of test substances, and 15 minutes, 30 minutes, 60 minutes and 120 minutes after the administration.

The results are expressed as mean and standard error. The significance of the mean was tested by the Dunnett's multiple test.

Experimental Results

The pain threshold at the von Frey test before dosing D-allose at the first test for examining the effect of D-allose was 4.4±0.3 g. Via the administration of D-allose at 1 g/kg, the pain threshold was not significantly different from that in the distilled water-dosed group. In the 3 g/kg D-allose-dosed group 15 minutes after the administration and in the 6 g/kg D-allose-dosed group 15 minutes, 30 minutes and 60 minutes after the administration, significant increase of the pain thresholds was observed, compared with the distilled water-dosed group (FIG. 1).

Figure 2:
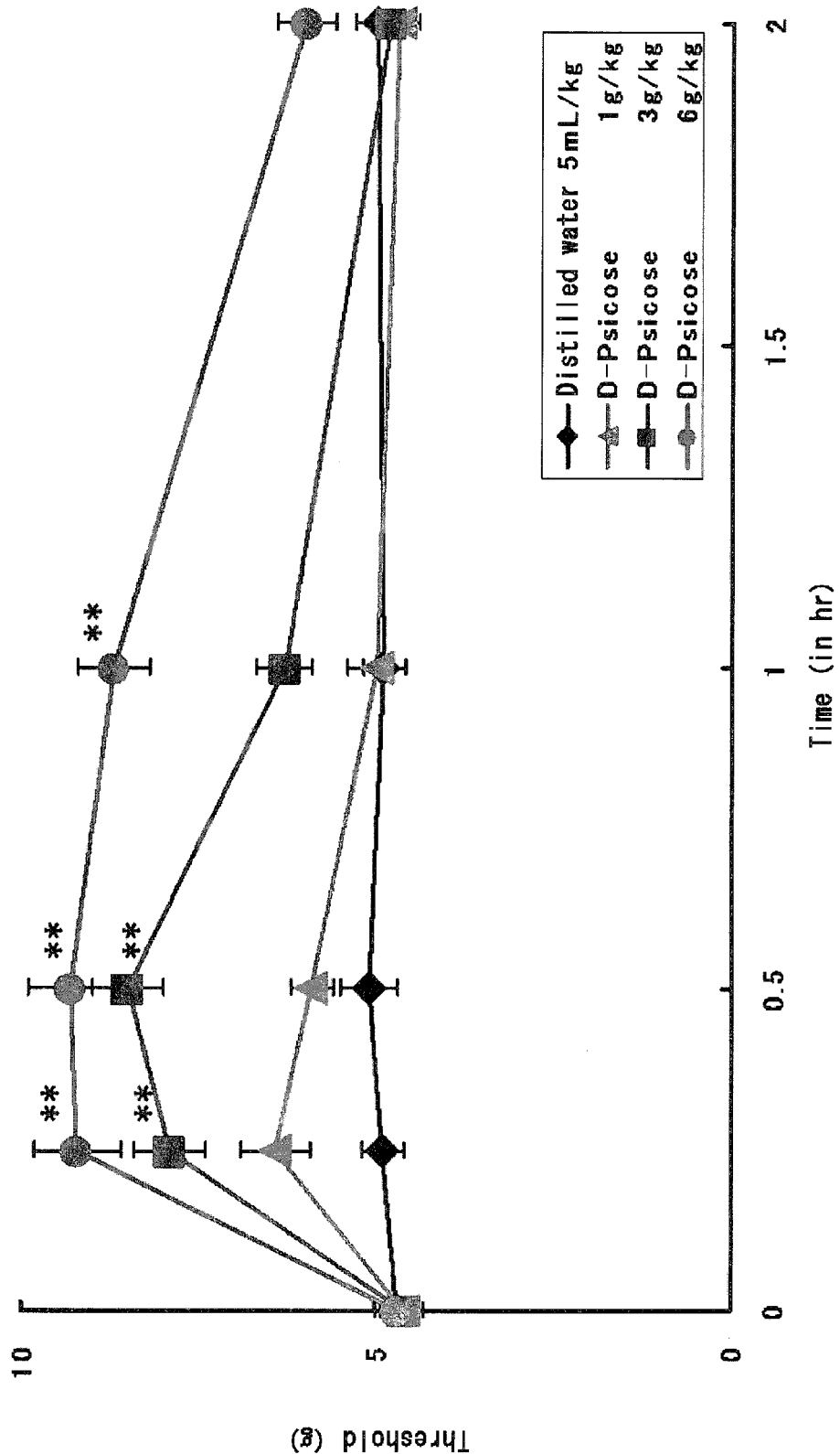
FIG. 2 Effect of D-psicose on the pain threshold in the Chung model rat [in the figure, ** means $p<0.01$ (vs distilled water 5 mL/kg), N=10]

The pain threshold at the von Frey test before dosing D-psicose at the second test for examining the effect of D-psicose was 4.7±0.3 g. Via the administration of D-psicose at 1 g/kg, the increase of the pain threshold was observed 15 minutes after the administration, but was not significantly different from that in the distilled water-dosed group. In the 3 g/kg D-psicose-dosed group 15 minutes and 30 minutes after the administration and in the 6 g/kg D-allose-dosed group 15 minutes, 30 minutes and 60 minutes after the administration, significant increase of the pain thresholds was observed, compared with the distilled water-dosed group (FIG. 2).

Figure 3:
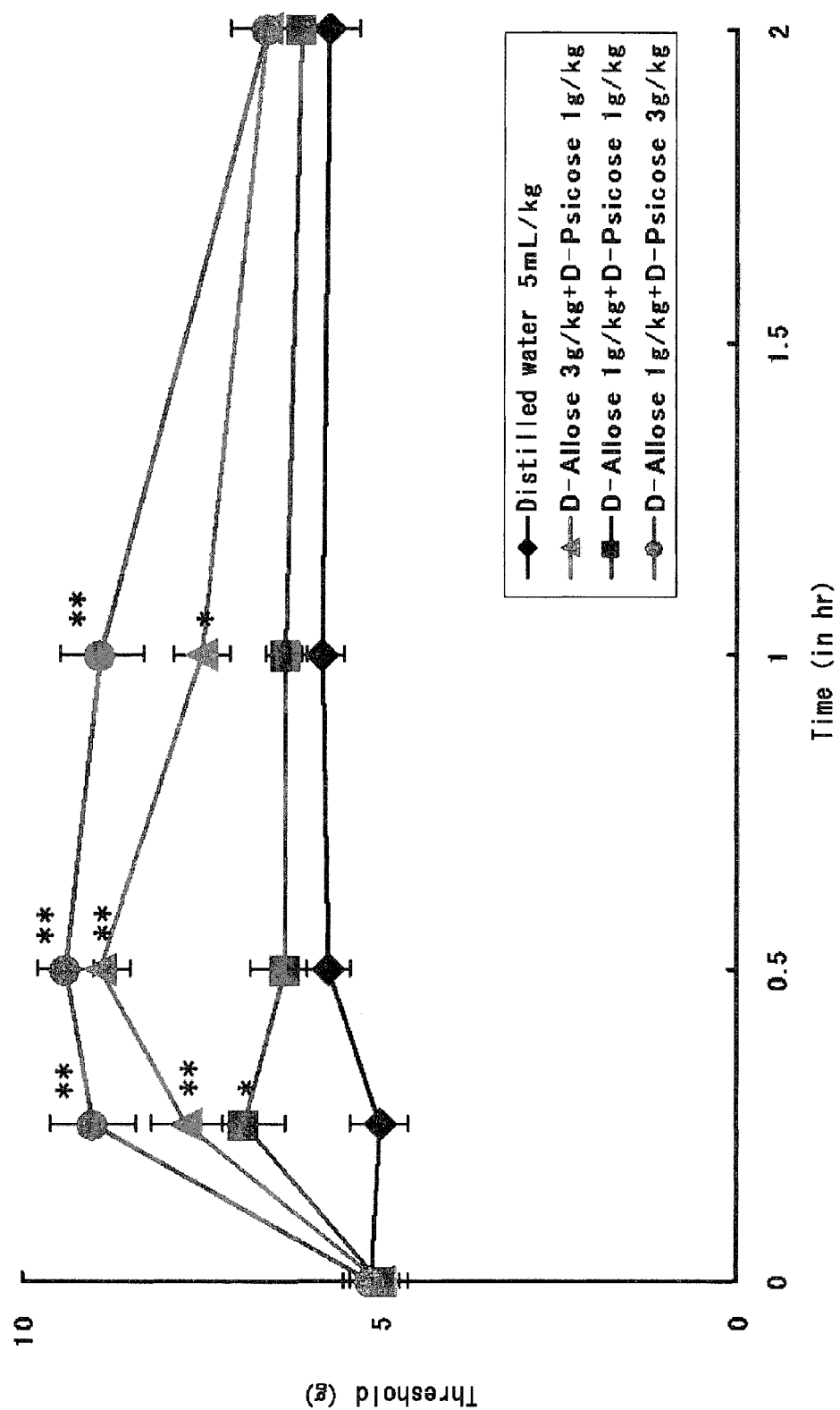
FIG. 3 Effects of D-allose and D-psicose in combination on the pain threshold in the Chung model rat [in the figure, * Hmeans $p<0.05$; ** means $p<0.01$ (vs distilled water 5 mL/kg), N=10]

The pain threshold at the von Frey test before dosing a mixture of D-allose and D-psicose at the third test for examining the effect of the mixture was 5.1±0.4 g. Via the administration of D-allose at 1 g/kg and D-psicose at 1 g/kg, significant increase of the pain threshold was observed 15 minutes after the administration. In a group administered with D-allose at 3 g/kg and D-psicose at 1 g/kg and in a group administered with D-allose at 1 g/kg and D-psicose at 3 g/kg, significant increase of the pain threshold was observed 15 minutes, 30 minutes and 60 minutes after the administration, compared with the distilled water-dosed group (FIG. 3).

No significant difference was observed among the pain thresholds in the grou
before the individual administrations of D-allose, D-psicose or the mixture of the two.

[Discussion]

Neuropathic pain indicates an abnormal state where a contact absolutely without any pain in general or temperature change is felt as pain or a stimulation never causing any sense of pain in general is felt as pain, so individuals with neuropathic pain have extremely low levels of QOL. It is considered that neuropathic pain occurs via some nerve damage. Plural mechanisms are suggested for the onset. Conditions emerging therefor are so complex that definite therapeutic methods have not yet been achieved. In such status, it is currently suggested that the development of therapeutic types as many as possible so as to cope with each condition is the best coping method with neuropathic pain. For that purpose, the development of drug types with different properties as many as possible as analgesics is required therefor.

The present research works were done for screening for an analgesic effect among rare sugars with unknown pharmacological properties, in sugars with no recognized analgesic effects. It was demonstrated that D-allose and D-psicose had effects on neuropathic pain.

Neuropathic pain models are frequently used as human neuralgia models for making research works on pain and screening for analgesics. Several types of neuropathic pain models are suggested, which individually have characteristic features (Bennett, G. J., and Xie, Y. K., Pain, 33, 87-107, 1988; Coderre, T. J., et al., Pain, 26, 61-84, 1986; Pain, 43, 205-218, 1990; Kim, S. H., and Chung, J. M., Pain, 50, 355-363, 1992). The Chung model as the neuropathic pain model used in the research works is a model with a characteristic feature such that the model is afflicted with a strong pain on contact stimulation, and is known that the model is annoyed with a pain very similar to human neuralgia (Exp. Brain Res., 113, 200-206, 1997). In such model, the von Frey test is frequently used so as to assay the pain intensity via contact. The von Frey test is a method for observing whether or not an animal when the footpad is pressed with a fine metal wire withdraws the leg. When the animal withdraws the leg, the force just pressing the footpad is defined the threshold then.

When any one of D-allose and D-psicose was given, the threshold was highly raised, in a manner proportional to the dose thereof. Compared with the administration of D-allose, however, the increase of the threshold via the administration of D-psicose was greater. Compared with the single administration of 3 g/kg D-allose or 1 g/kg D-psicose, the simultaneous administration of 3 g/kg D-allose and 1 g/kg D-psicose increased more the pain threshold and prolonged the time for the increase sustained. The enhancement of the effect increasing the threshold due to combination of D-allose and D-psicose was observed. The same tendency was observed in case of the combined use of 1 g/kg D-allose and 3 g/kg D-psicose.

A larger pain threshold means that pain is more hardly felt. In accordance with the invention, therefore, the analgesic effects of the single administration of D-allose or D-psicose and the simultaneous administration of D-allose and D-psicose were demonstrated. This indicates that D-allose and D-psicose have a therapeutic effect on neuropathic pain. So far, not any sugar with an analgesic effect has been found. Therefore, the results of the research works suggest a possibility of the development of a novel type of a therapeutic agent with a sugar structure and with a therapeutic effect on neuropathic pain.

INDUSTRIAL APPLICABILITY

Pain mitigation is the most essential clinical application. Even currently with the progress in medicine, it is known that a certain type of pain is hardly mitigated. The neuropathic pain for which the invention is disclosed in the present patent is a pain hardly mitigated. It is said that pain from cancer at the terminal stage and pain due to neuritis as a complication of diabetes mellitus, for example, are hardly tolerable. The modern medicine is powerless to such pain. The composition disclosed in the invention is effective for neuropathic pain and is additionally quite safe without any toxicity. Therefore, the composition will highly possibly be applied to the mitigation of the pain for which no therapeutic approach has existed so far.

The invention claimed is:

1. A method for eliminating, mitigating or reducing neuropathic pain in a patient afflicted with neuropathic pain, comprising:
   administering a composition containing a mixture of (i) D-allose or a D-allose derivative and (ii) D-psicose or a D-psicose derivative to said patient in need of eliminating, mitigating or reducing the neuropathic pain,
   wherein in said mixture, a ratio of (i) D-allose or a D-allose derivative to (ii) D-psicose or a D-psicose derivative is 1:3.

2. The method of claim 1, wherein said composition contains said mixture at 0.01 to 90% by weight.

3. The method of claim 1 or 2, wherein the daily dose of said mixture is 0.01 to 100 g.

4. The method of claim 1 or 2, wherein the neuropathic pain is a neuropathic pain due to a disease selected from the group consisting of trigeminal neuralgia, post-surgery pain, periodontitis, gingivitis, gingivostomatitis, oral ulcer, herpes zoster, postherpeutic neuralgia, diabetic neuralgia, causalgia, phantom limb pain and cancer pain.

* * * * *